United States Patent [19]

Soost et al.

[11] Patent Number: Plant 6,001

[45] Date of Patent: Sep. 1, 1987

[54] GRAPEFRUIT HYBRID NAMED MELOGOLD

[75] Inventors: Robert K. Soost; James W. Cameron, both of Riverside, Calif.

[73] Assignee: The Regents of the University of California, Berkeley, Calif.

[21] Appl. No.: 797,286

[22] Filed: Nov. 12, 1985

[51] Int. Cl.[4] ..... A01H 5/03

[52] U.S. Cl. ..... Plt./45

[58] Field of Search ..... Plt./45

*Primary Examiner*—Robert E. Bagwill

*Attorney, Agent, or Firm*—Townsend and Townsend

[57] ABSTRACT

A new and distinct variety of grapefruit hybrid citrus tree characterized by a maturity habit a full six months earlier than grapefruit grown in the same areas and further characterized by its nearly seedless white-fleshed fruit which is sometimes slightly bitter and has a flavor similar to 'Oroblanco' but more like pummelo. Fruit is tender and juicy and flesh separates will from segment membranes.

2 Drawing Figures

This invention relates to a new and distinct variety of grapefruit hybrid plant characterized by early maturity habit when grown in the inland citrus areas of California such as Riverside and Lindcove where fruit matures several months earlier than present grapefruit cultivars.

The variety is further characterized by its fruit which resembles that of present white-fleshed grapefruit cultivars. Its flesh is tender and juicy, separating well from segment membranes. The flavor of the fruit of the new variety called 'Melogold' is very close to 'Oroblanco,' U.S. Plant Pat. No. 4,645, but has a flavor different from both 'Oroblanco' and grapefruit and is more like pummelo.

Figure 1:
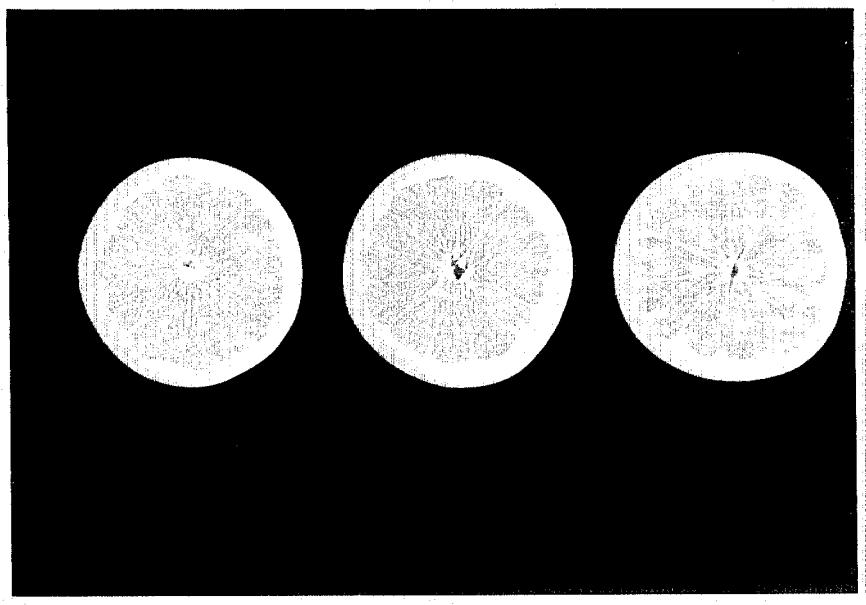
Figure 2:
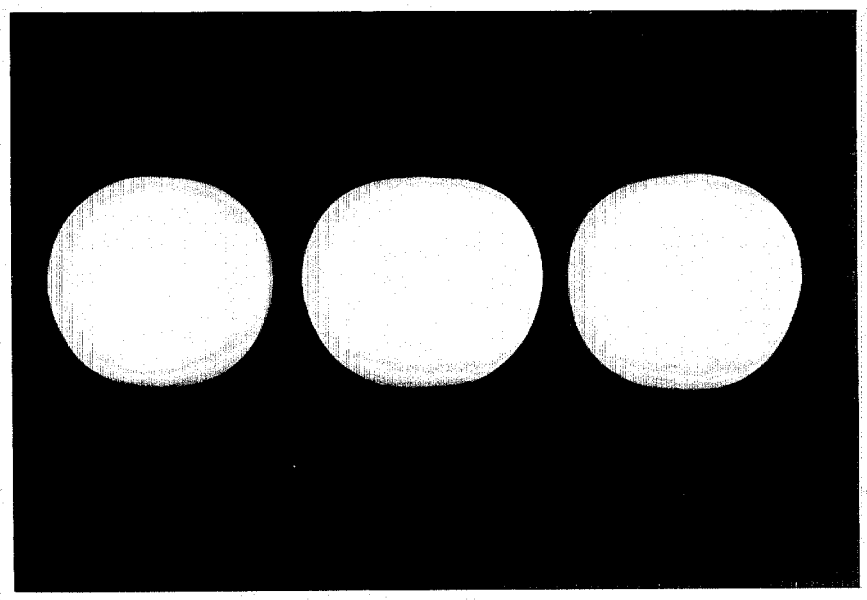

FIG. 1 of the accompanying drawing illustrates cut [and whole] fruit of 'Melogold,' 'Oroblanco' and 'Marsh' (left to right) and FIG. 2 illustrates whole fruit of 'Melogold,' 'Oroblanco' and 'Marsh' (left to right). Fruits were selected for equal size. 'Melogold' as shown in the drawing is therefore smaller than its average size.

The variety of this invention is the result of a cross made in 1958 between an essentially acidless pummelo, CRC 2240 (*Citrus grandis* Osbeck), which had been shown to impart low acidity to its progenies, and a seedy, white tetraploid grapefruit (*Citrus paradisi* Macf.). The small population from this cross consisted of one tetraploid and six triploids, which were field planted in 1962. Two of the triploids had particularly favorable characteristics and were propagated for further testing. One of these was 'Oroblanco.' The second, tested as 6C26,18, is the variety of this application called 'Melogold.' Observations of the new variety have been made and data collected at Riverside since 1967. Additional test trees were planted at the University of California, Lindcove Field Station, Southcoast Field Station, and at the U.S. Date and Citrus Station, Indio, Calif.

Early maturity is the outstanding characteristic of 'Melogold.' It matures in early November at Lindcove and by December at Riverside, fully six months ahead of grapefruit grown in the same areas. It would provide an early maturing grapefruit type for the interior valley areas of California and other areas with similar environments. Its maturity period coincides with the grapefruit harvest period of desert valley areas of California and Arizona. However, its ratio of soluble solids to acid is much higher than the commercial grapefruit from these areas. 'Melogold' does not appear to be suitable for the desert areas, nor for the coastal areas. 'Melogold' is commercially seedless, and very mild in flavor.

'Melogold' has been grown only on Troyer citrange and Rough lemon rootstocks. The oldest trees on Troyer were 17 years old when pulled and showed no signs of bud union difficulties or decline. Existing trees on Troyer are now 12 years old. Rough lemon is not recommended because of its adverse effects on fruit quality. Other rootstocks that are compatible with grapefruit may be suitable for 'Melogold.'

Budwood of 'Melogold' has been indexed for and found free of graft transmissible diseases. A primary budwood source is maintained in the screen house quarantine facilities of the Citrus Clonal Protection Program (CCPP) at Riverside. A field source is available in the CCPP foundation planting at Lindcove Field Station. The index number is V.I. 323.

The general characteristics of the fruit of the new variety resemble those of present white-fleshed grapefruit cultivars, but are more pummelo-like than 'Oroblanco.' Fruit size is larger than 'Marsh' grapefruit and 'Oroblanco' at all test locations. Fruit weight at Riverside from 1967 through 1975 averaged 470 G. for 'Melogold,' 360 G. for 'Oroblanco,' and 280 G. for 'Marsh.' At Lindcove, from 1975 through 1983 with younger trees, fruit weight has averaged 700, 520, and 450 G., respectively, for the three cultivars.

Fruit shape is comparable to 'Marsh' and 'Oroblanco' with a slight tendency to obconate. Exterior peel color is slower to develop than 'Marsh' grapefruit, but late in the season is comparable. Exterior peel texture is smooth to slightly pebbled. Average peel thickness is slightly greater than 'Marsh,' but as a percentage of fruit diameter is equal to 'Marsh' and thinner than 'Oroblanco;' interior color and texture are the same as 'Oroblanco.' As with 'Oroblanco' the central core hollow is greater than 'Marsh' at maturity. The flesh is tender and juicy, separating well from segment membranes. Percent juice has been equal to 'Marsh' and slightly higher than 'Oroblanco.'

'Melogold' may have a slight bitterness, particularly early and late in the harvest season. In taste tests, 'Melogold' has always been preferred by a wide margin over 'Marsh,' but usually was a very close second to 'Oroblanco.' The flavor of 'Melogold' differs from both 'Oroblanco' and grapefruit, and is more like pummelo.

Total soluble solids, titratable acid, and solids-acid ratios of 'Melogold,' 'Oroblanco,' and 'Marsh' for years of record at Riverside and Lindcove, are shown in Tables 1 and 2 set forth as follows:

TABLE 1

| (Riverside) Year* | 'Melogold' | 'Oroblanco' | 'Marsh' |
|---|---|---|---|
| | Total soluble solids (%) | | |
| 1967 | 13.3 | 13.2 | 10.7 |
| 1969 | 13.6 | 12.9 | 11.5 |
| 1970 | 11.0 | 11.4 | 8.5 |
| 1971 | 13.4 | 13.8 | 10.4 |
| 1972 | 12.8 | 13.5 | 9.3 |
| 1973 | 13.0 | 14.0 | 10.6 |
| 1974 | 10.4 | 10.8 | 9.4** |
| 1975 | 11.8 | 12.3 | 9.9 |
| 1976 | 8.6 | 8.7 | 9.5 |
| 1977 | 8.9 | 9.8 | — |
| 1978 | 10.4 | 13.1 | — |
| | Acid (%) | | |
| 1967 | 1.09 | 1.22 | 2.16 |
| 1969 | 0.90 | 1.20 | 2.07 |
| 1970 | 1.02 | 1.26 | 1.95 |
| 1971 | 1.23 | 1.61 | 2.02 |
| 1972 | 0.98 | 1.06 | 1.62 |
| 1973 | 1.21 | 1.40 | 2.25 |
| 1974 | 0.90 | 0.91 | 1.47** |
| 1975 | 1.10 | 1.24 | 2.22 |
| 1976 | 0.85 | 0.92 | 1.73 |
| 1977 | 0.87 | 0.87 | — |
| 1978 | 0.77 | 0.85 | — |
| | Solids:Acid (%) | | |
| 1967 | 12.2 | 10.8 | 4.9 |
| 1969 | 15.1 | 10.8 | 5.6 |
| 1970 | 10.8 | 9.0 | 4.4 |
| 1971 | 10.9 | 8.6 | 5.1 |
| 1972 | 13.1 | 12.7 | 5.7 |
| 1973 | 10.7 | 10.0 | 4.7 |
| 1974 | 11.6 | 11.9 | 6.4** |
| 1975 | 10.7 | 9.9 | 4.5 |
| 1976 | 10.1 | 9.4 | 5.5 |
| 1977 | 10.2 | 11.3 | — |
| 1978 | 13.5 | 15.4 | — |

*All samples harvested in mid-December, unless otherwise noted.
**January 1975 samples.

TABLE 2

| (Lindcove) Year* | 'Melogold' | 'Oroblanco' | 'Marsh' |
|---|---|---|---|
| | Total soluble solids (%) Data by years | | |
| 1975 | 10.2 | 12.2 | 9.2** |
| 1976 | 10.2 | 10.7 | — |
| 1977 | 11.0 | 11.7 | 11.3 |
| 1978 | 10.0 | 10.4 | 9.7*** |
| 1980 | 10.7 | 10.8 | — |
| 1981 | 11.7 | 11.0 | — |
| 1982 | 11.1 | 10.4 | 9.8*** |
| 1983 | 11.4 | 9.8 | 8.9*** |
| | Data during 1982 season | | |
| 12-9-81 | 11.7 | 11.0 | — |
| 1-20-82 | 12.0 | 11.2 | — |
| 2-25-82 | 12.1 | 11.9 | — |
| 3-16-82 | 11.5 | 11.1 | 9.8 |
| | Acid (%) Data by years | | |
| 1975 | 1.14 | 1.07 | 1.61** |
| 1976 | 0.99 | 0.86 | — |
| 1977 | 0.96 | 1.05 | 1.82 |
| 1978 | 0.91 | 0.82 | 1.63*** |
| 1980 | 1.05 | 0.98 | — |
| 1981 | 0.84 | 0.84 | — |
| 1982 | 0.93 | 0.96 | 1.47*** |
| 1983 | 0.91 | 0.89 | 1.44*** |
| | Data during 1982 season | | |

TABLE 2-continued

| (Lindcove) Year* | 'Melogold' | 'Oroblanco' | 'Marsh' |
|---|---|---|---|
| 12-9-81 | 0.84 | 0.84 | — |
| 1-20-82 | 0.86 | 0.84 | — |
| 2-25-82 | 0.74 | 0.76 | — |
| 3-16-82 | 0.74 | 0.79 | 1.5 |
| | Solids:Acid (%) Data by years | | |
| 1975 | 8.9 | 11.4 | 5.7** |
| 1976 | 10.3 | 12.4 | — |
| 1977 | 11.5 | 11.1 | 6.2 |
| 1978 | 11.0 | 12.7 | 5.9*** |
| 1980 | 10.2 | 11.0 | — |
| 1981 | 13.9 | 13.1 | — |
| 1982 | 11.9 | 10.8 | 6.7*** |
| 1983 | 12.5 | 11.0 | 6.2*** |
| | Data during 1982 season | | |
| 12-9-81 | 13.9 | 13.1 | — |
| 1-20-82 | 13.9 | 13.3 | — |
| 2-25-82 | 16.3 | 15.7 | — |
| 3-16-82 | 15.5 | 14.0 | 6.5 |

*Samples harvested in mid-December, unless otherwise noted.
**January samples, the year following the listed year.
***March samples, the year following the listed year.

The data for Riverside for 'Melogold' and 'Oroblanco,' through 1975, are from the original seedling trees or the first-budded trees on Troyer citrange [*Citrus sinensis* (L.) Osbeck×*Poncirus trifoliata* (L.) Raf.] rootstock. The slightly lower solids and acids in 1976 through 1978 are from younger trees also on Troyer citrange. All trees at Lindcove are also on Troyer citrange. At Riverside, solids have consistently been slightly lower than 'Oroblanco,' but at Lindcove they have sometimes been slightly higher. Acidity at Riverside has also been consistently slightly lower than 'Oroblanco,' but has fluctuated at Lindcove. As with 'Oroblanco,' acidity is much lower than 'Marsh' at all sampling dates through the season at all test locations.

Data for 1981–82 season at Lindcove are shown above in Table 2. The low acidity with moderate solids produces a ratio that is much higher than 'Marsh' at all sampling dates. Fruit from Coachella Valley and Southcoast Field Station also have acidity and moderate solids even early in the season. However, fruit from Coachella Valley have been rather insipid, and fruit from Southcoast Field Station generally have been slightly bitter and lacking in flavor.

A long term yielding behavior of the new variety is uncertain. Test trees at Riverside have had moderate to heavy yields with a tendency to alternate. Even with heavy yields, fruit size has been considerably larger than 'Marsh.'

The new variety is described as follows:

Tree: Vigorous, dense, slightly drooping branches, many short, fine thorns in leaf axils. Fruits borne singly or in clusters, much inside fruit.

Leaves: Large (ave. 116×67 mm), thick, ovate; apex acute; base rounded; edges slightly crenate, finely serrulate. Petioles articulate, winged (ave. 10×14 mm), entire. Mature leaves and twigs glabrous, upper surface glossy dark green, lower surface light green; young shoots, ovaries and very young fruit slightly pubescent.

Fruit: Slightly oblate to slightly obovoid with no neck; base depressed but smooth; stylar scar depressed. Ave. length 10–12 cm, ave. width 12–14 cm. Ave. weight 550 gm. Nearly seedless. Rind grained; oil glands small (<1 to 1.5 mm), slightly depressed, color darker than rind. Rind color light yellow, darkening as maturity progresses (Munsell 2.5 GY 8/6 to 5 Y 9/9). Rind thickness variable, ave. 10–12 mm. Interior segments usually 13 to 16; segment membranes medium thickness. Pulp color very pale yellow (Munsell 5 Y 9/4 to 7.5 Y 9/4). Pulp vesicles medium, tender, variable shape, juicy. Aroma pleasant, grapefruit-like.

Season of use: San Joaquin Valley — November to February, Riverside — December to April.

Ratios: Soluble solids 9 to 12 percent; % acid, 1.20 to 0.70; solids: acid ratio, 9.0 to 12.0; ascorbic acid level similar to and not lower than present commercial grapefruit cultivars (30 to 40 mg per 100 ml).

We claim:

1. The new and distinct variety of grapefruit hybrid plant herein described and illustrated and identified by the characteristics enumerated above.

* * * * *